(12) United States Patent
Lin et al.

(10) Patent No.: US 11,921,090 B2
(45) Date of Patent: Mar. 5, 2024

(54) WHOLE-VEHICLE-BASED METHOD FOR EVALUATING EXTREME PRESSURE AND ANTIWEAR PROPERTIES OF GREASE

(71) Applicant: Guangxi Liugong Machinery Co., Ltd., Liuzhou (CN)

(72) Inventors: Bo Lin, Liuzhou (CN); Li Zhang, Liuzhou (CN); Xiaona Wan, Liuzhou (CN); Jie Shao, Liuzhou (CN); Huiliang Xin, Liuzhou (CN); Hao Liang, Liuzhou (CN); Jinqiong Luo, Liuzhou (CN); Mingfeng Tan, Liuzhou (CN); Mingzhi Lin, Liuzhou (CN); Guoqing Hou, Liuzhou (CN)

(73) Assignee: Guangxi Liugong Machinery Co., Ltd. (CN)

( * ) Notice: Subject to any disclaimer, the term of this patent is extended or adjusted under 35 U.S.C. 154(b) by 259 days.

(21) Appl. No.: 17/604,374

(22) PCT Filed: Apr. 17, 2020

(86) PCT No.: PCT/CN2020/085250
§ 371 (c)(1),
(2) Date: Oct. 15, 2021

(87) PCT Pub. No.: WO2020/211830
PCT Pub. Date: Oct. 22, 2020

(65) Prior Publication Data
US 2022/0196531 A1    Jun. 23, 2022

(30) Foreign Application Priority Data

Apr. 19, 2019 (CN) .......................... 201910319268.4

(51) Int. Cl.
*G01N 3/56* (2006.01)
*G01N 33/30* (2006.01)

(52) U.S. Cl.
CPC .............. *G01N 3/56* (2013.01); *G01N 33/30* (2013.01); *G01N 2203/003* (2013.01); *G01N 2203/0058* (2013.01)

(58) Field of Classification Search
CPC ....................................................... G01N 3/56
(Continued)

(56) References Cited

U.S. PATENT DOCUMENTS

2003/0101793 A1    6/2003    Evans

FOREIGN PATENT DOCUMENTS

| CN | 2557306 Y | 6/2003 |
|---|---|---|
| CN | 102829962 A | 12/2012 |

(Continued)

OTHER PUBLICATIONS

Ando. Transmation of JP-2008151691-A. Published Jul. 2008. Accessed Aug. 2023. (Year: 2008).*

(Continued)

*Primary Examiner* — Walter L Lindsay, Jr.
*Assistant Examiner* — Philip T Fadul
(74) *Attorney, Agent, or Firm* — Dickinson Wright PLLC

(57) ABSTRACT

A whole-vehicle-based method for evaluating extreme pressure and antiwear properties of grease includes injecting the grease onto a key bearing pin and causing the engineering machine to operate without load is disclosed. The method includes causing the engineering machine to operate under a load of 10% to 150% rated load at least once, viewing and analyzing a wear condition of a surface of the bearing pin, and issuing a whole-vehicle-based evaluation report of extreme pressure and antiwear properties of grease. The engineering machine is caused to operate once under a load of 10% to 150% rated load for 0.5 min to 100 h.

10 Claims, 4 Drawing Sheets

(58) Field of Classification Search
USPC .................................................. 73/10
See application file for complete search history.

(56) References Cited

FOREIGN PATENT DOCUMENTS

| | | | |
|---|---|---|---|
| CN | 103901184 A | | 7/2014 |
| CN | 203772863 U | | 8/2014 |
| CN | 204101435 U | | 1/2015 |
| CN | 204214758 U | | 3/2015 |
| CN | 204514783 U | | 7/2015 |
| CN | 107340087 A | | 11/2017 |
| CN | 207181261 U | | 4/2018 |
| CN | 207379897 U | | 5/2018 |
| CN | 207992212 U | | 10/2018 |
| CN | 109238713 A | | 1/2019 |
| CN | 208488322 U | | 2/2019 |
| CN | 109991112 A | | 7/2019 |
| JP | 2003344254 A | | 12/2003 |
| JP | 2008151691 A | | 7/2008 |
| JP | 2008151691 A | * | 7/2008 |
| JP | 2015031518 A | | 2/2015 |
| WO | 0127642 A1 | | 4/2001 |
| WO | 2014179537 A1 | | 11/2014 |

OTHER PUBLICATIONS

Liang et al. "Performance comparison and application research of excavator lubricating grease (translation)." Runhuayou, vol. 32, No. 6. Dec. 2017. p. 14-18. (Year: 2017).*

Pearson et al. "Development of fatigue monitoring system for a hydraulic excavator." Practice periodical on structural design and construction 9.4 (2004): 221-226. (Year: 2004).*

European Search Report for EP Application No. 20791410.2, dated Nov. 25, 2022, pp. 1-48.

International Search Report with English Translation for PCT Application No. PCT/CN2020/085250, dated Jul. 15, 2020, 5 pages.

Fan, "Discussion on Evaluation Method of Friction and Wear Performance of Low Speed Heavy Duty Petroleum Special Bearing Grease," Petroleum Products Application Research, Dec. 31, 2009, pp. 43-47, vol. 6, China Academic Journal Electronic Publishing House, http://www.cnki.net.

Sheng et al., "Experimental Study on the Effect of Particle Contaminant on Anti-wear Performance of Lubricating Oils," Lubrication Engineering, Jul. 2017, pp. 7-13, vol. 42, No. 7, China Academic Journal Electronic Publishing House, http://www.cnki.net.

Chen et al., "Anti-wear property of Self-repairing Mineral Particles as Grease Lubricant Additives on the Metal Friction Pairs," Advanced Materials Research, 2010, pp. 1459-1462, , vols. 97-101, Trans Tech Publications, Switzerland, doi:10.4028/www.scientific.net/AMR.97-101.1459.

Liang et al., "Performance Comparison and Application Research on Grease for Excavator," Lubricating Oil, Dec. 2017, pp. 14-18, vol. 32, No. 6, China Academic Journal Electronic Publishing House, http://www.cnki.net.

Yang et al., "Study on Anti-Wear for the Lithium Complex Grease," Acta Petrolei Sinica (Petroleum Processing Section), Oct. 17, 2011, pp. 71-75, China Academic Journal Electronic Publishing House, http://www.cnki.net.

Chang et al., "Anti-Wear and Friction Properties of Nanoparticles as Additives in the Lithium Grease," International Journal of Precision Engineering and Manufacturing, Oct. 2014, pp. 2059-2063, vol. 15, No. 10, KSPE and Springer, doi:10.1007/s12541-014-0563-y.

* cited by examiner

WHOLE-VEHICLE-BASED METHOD FOR EVALUATING EXTREME PRESSURE AND ANTIWEAR PROPERTIES OF GREASE

CROSS-REFERENCE TO RELATED APPLICATION(S)

This is a national stage application filed under 37 U.S.C. 371 based on International Patent Application No. PCT/CN2020/085250, filed Apr. 17, 2020, which claims priority to Chinese Patent Application No. 201910319268.4 filed with the China National Intellectual Property Administration (CNIPA) on Apr. 19, 2019, the disclosures of which are incorporated herein by reference in its entirety.

TECHNICAL FIELD

The present application relates to the field of testing extreme pressure and antiwear properties of grease, for example, a whole-vehicle-based method for evaluating extreme pressure and antiwear properties of grease.

BACKGROUND

Methods for evaluating extreme pressure and antiwear properties of grease at home and abroad mainly include the four-ball method and the Timken method. In the Timken method, the test material includes a steel ring and a steel block, the rotational speed of the test shaft is 800 r/min±5 r/min, the load is 0 to 270 N, and the contact form of the friction pair is linear friction. In the four-ball method, the test material includes steel balls, the rotational speed is 1770 r/min, the load is 0 to 7846 N, and the contact form of the friction pair is point friction.

In the related art, the evaluation method of extreme pressure and antiwear properties of grease cannot be fully applied to working conditions such as low speed, heavy load and impact load. Grease tested by the four-ball tester and the Timken tester may also have the problems of abnormal wear, wear failure, and an abnormal noise in practical application.

SUMMARY

The present application provides a whole-vehicle-based method for evaluating extreme pressure and antiwear properties of grease. A test method, in which an engineering machine as a whole vehicle is used, is used to evaluate extreme pressure and antiwear properties of grease so the reliability of the test is high.

A whole-vehicle-based method for evaluating extreme pressure and antiwear properties of grease is provided in an embodiment. The method includes: injecting the grease onto a key bearing pin of an engineering machine and causing the engineering machine to operate without load; causing the engineering machine to operate under a load of 10% to 150% rated load at least once; viewing and analyzing a wear condition of a surface of the bearing pin; and issuing a whole-vehicle-based evaluation report of extreme pressure and antiwear properties of grease.

The engineering machine is caused to operate once under a load of 10% to 150% rated load for 0.5 min to 100 h.

A whole-vehicle-based method for evaluating extreme pressure and antiwear properties of grease is provided in an embodiment. The method includes: selecting an engineering machine and a key bearing pin of the engineering machine; injecting the grease onto the key bearing pin and commissioning the key bearing pin; causing the engineering machine to operate effectively under no load and under a load of 10n % to (10n±2)% rated load separately; viewing and analyzing a wear condition of a surface of the bearing pin; and issuing a report of extreme pressure and antiwear properties of grease.

n denotes an integer of 1 to 15. The engineering machine is caused to operate once under a load of 10n % to (10n±2)% rated load for 0.5 min to 100 h.

A whole-vehicle-based method for evaluating extreme pressure and antiwear properties of grease is provided in an embodiment. The method includes: injecting the grease onto a key bearing pin of an engineering machine and causing the engineering machine to operate without load; causing the engineering machine to operate under a load of 10% to 150% rated load at least once; recording whether an abnormal noise occurs during effective operation of the engineering machine under different loads; and recording a whole-vehicle-based evaluation report of extreme pressure and antiwear properties of grease according to a recorded result.

The engineering machine is caused to operate once under a load of 10% to 150% rated load for 0.5 min to 100 h.

A whole-vehicle-based method for evaluating extreme pressure and antiwear properties of grease is provided in an embodiment. The method includes: selecting an engineering machine and a key bearing pin of the engineering machine; injecting the grease onto the key bearing pin and commissioning the key bearing pin; causing the engineering machine to operate effectively under no load and under a load of 10n % to (10n±2)% rated load separately; recording whether an abnormal noise occurs during effective operation of the engineering machine under different loads; and recording a whole-vehicle-based evaluation report of extreme pressure and antiwear properties of grease according to a recorded result.

n denotes an integer of 1 to 15. The engineering machine is caused to operate once under a load of 10n % to (10n±2)% rated load for 0.5 min to 100 h.

DETAILED DESCRIPTION

For purposes of the following detailed description, it should be understood that the present application may assume various alternative variations and step sequences unless expressly stated to the contrary. In addition, unless used in any operation example or otherwise indicated, all numbers indicating the amounts of components used in, for example, the description and the claims should be understood as being modified by the term "about" in all cases. Therefore, unless indicated to the contrary, the numerical parameters set forth in the following description and the appended claims are approximations that vary in accordance with the desired performance to be obtained in the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that numerical ranges and parameters setting forth the broad scope of the present application are approximations, the numerical values set forth in the specific examples are reported as precisely as possible. Any numerical value, however, inherently contains certain errors necessarily resulting from the standard deviation found in their respective testing measurements.

Also, it should be understood that any numerical range recited herein is intended to include all sub-ranges subsumed therein. For example, the range of 1 to 10 is intended to include all sub-ranges between (and inclusive of) the minimum value 1 and the maximum value 10, that is, have the minimum of values equal to or greater than 1 and the maximum of values equal to or less than 10.

Figure 4:
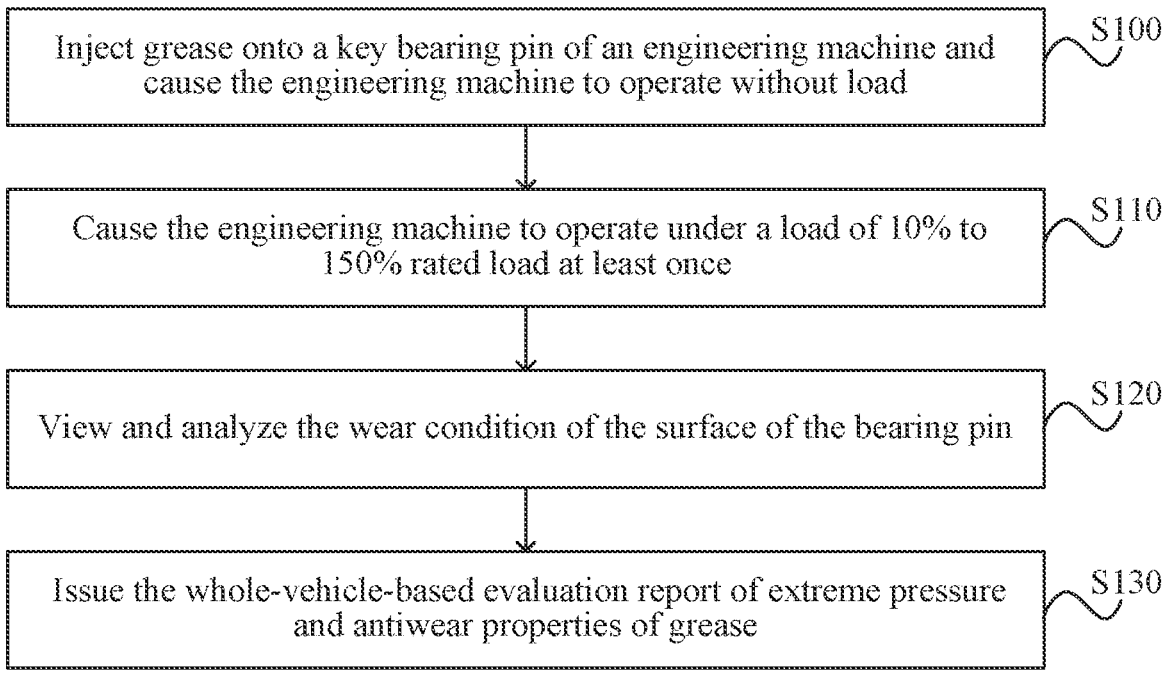
FIG. 4 is a flowchart illustrating a whole-vehicle-based method for evaluating extreme pressure and antiwear properties of grease according to an embodiment.

As illustrated in FIG. 4, a whole-vehicle-based method for evaluating extreme pressure and antiwear properties of grease according to the present application includes the steps described below.

In S100, the grease is injected onto the key bearing pin of the engineering machine, and the engineering machine is caused to operate without load.

In S110, the engineering machine is caused to operate under a load of 10% to 150% rated load at least once.

The operating time is 0.5 min to 100 h.

In S120, the wear condition of the surface of the bearing pin is viewed and analyzed.

In S130, the whole-vehicle-based evaluation report of extreme pressure and antiwear properties of grease is issued.

In the present application, the operation of the engineering machine is lifting configured weights. Any engineering machine well known to those skilled in the art can be selected, including an excavator, a crane, a forklift truck or a loader.

The bearing pin described in the present application is a mechanical term. The preparation material of the bearing pin (taking a loader as an example) is described in Table 1 below.

TABLE 1

Material of bearing pin

| Material of Pin | Material of Sleeve |
| --- | --- |
| 40Cr | 45/20CrMnTi |

The materials in Table 1 are the material of the pin and the material of the sleeve used in the present application. In fact, there may be many kinds of materials for the pin and the sleeve. The material of the pin may be, for example, 40MnB, 40Cr, 40CrMo, 45#, 35 # or non-quenched and tempered steel. The material of the sleeve may be, for example, 45#, 20CrMnTi, honeycomb sleeve, nylon sleeve, powder metallurgy oil-retaining sleeve, copper-based embedded graphite sleeve or zinc-based embedded graphite sleeve.

In the present application, the operating time of the engineering machine under the preset load of configured weights may be adjusted according to the weight of the engineering machine. The conventional effective operating time under a load of 10% to 150% rated load is generally 0.5 to 30 min. However, when the rated load of the engineering machine is relatively small and extreme pressure and antiwear properties of grease is relatively high, extreme pressure and antiwear properties of grease can be denoted by extending the effective operating time of the engineering machine under a load of 10% to 150% rated load. Exemplarily, the operating time of the engineering machine within the range of 0.5 min to 100 h.

Figure 5:
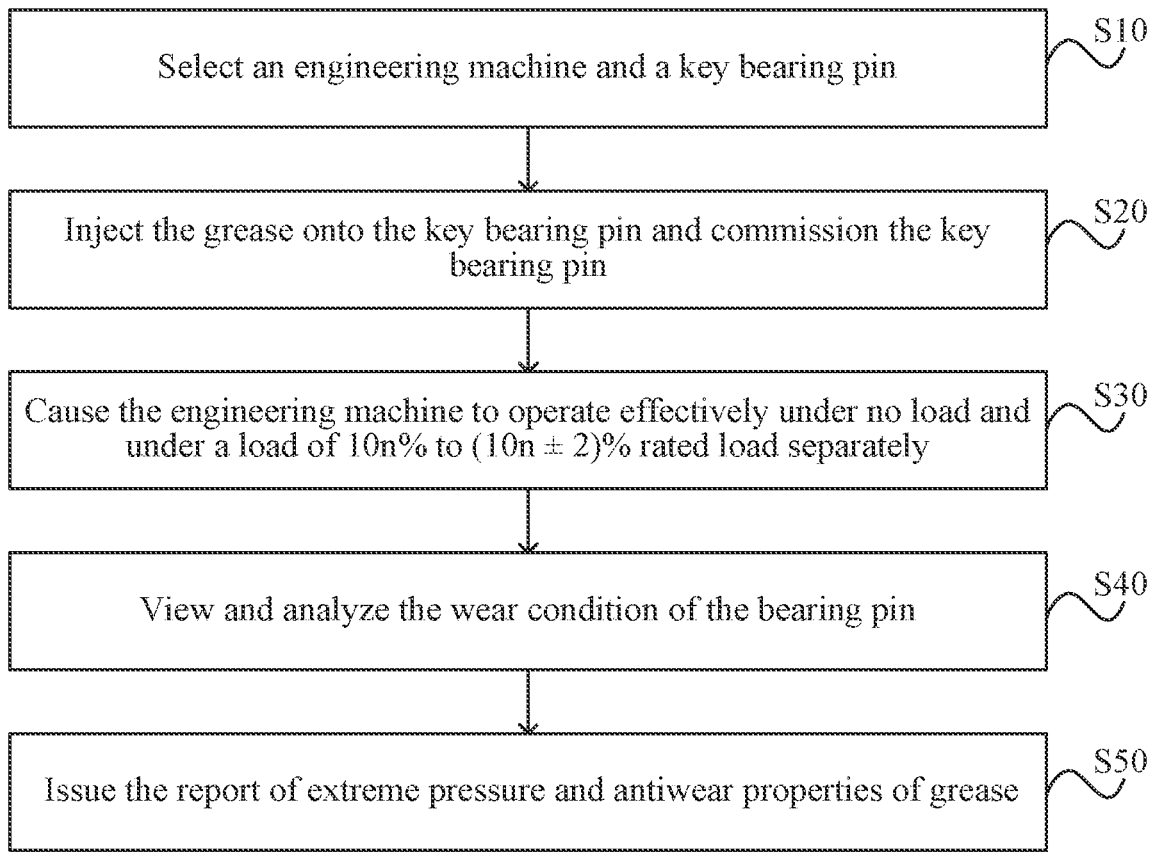
FIG. 5 is a flowchart illustrating a whole-vehicle-based method for evaluating extreme pressure and antiwear properties of grease according to an embodiment.

As illustrated in FIG. 5, in some embodiments, a range of the rated load of the engineering machine is 0.1 to 80 tons.

In an embodiment, the whole-vehicle-based method for evaluating extreme pressure and antiwear properties of grease includes the steps described below.

In S10, the engineering machine and the key bearing pin are selected.

In S20, the grease is injected onto the key bearing pin and the key bearing pin is commissioned.

The key bearing pin is commissioned after injecting the grease to make the grease evenly distributed.

In S30, the engineering machine is caused to operate effectively under no load and under a load of 10n % to (10n±2)% rated load separately.

In S40, the wear condition of the key bearing pin is viewed and analyzed.

In S50, the evaluation report of extreme pressure and antiwear properties of grease is issued.

n denotes an integer of 1 to 15.

In this scheme, the operating steps of commissioning the engineering machine and commissioning the key bearing pin can be added between the S10 and the S20 to ensure the normal operation of the device.

The key bearing pin described in the present application refers to the bearing pin that bears the largest weight and is most likely to be scratched due to friction during the effective operation of the engineering machine. Taking the loader as the example, the key bearing pins are the joint between the movable arm and the front frame, the joint between the movable arm cylinder and the front frame, and the joint between the movable arm and the movable arm cylinder, that is, point A, point S, and point Q in FIG. 3 respectively. After the experiment, point Q is disassembled to observe the wear condition on the surface of the pin. Therefore, in the process of evaluating extreme pressure and antiwear properties of grease, the engineering machine and the measuring point (the key bearing pin) are first selected, then the grease is injected onto the key bearing pin, and extreme pressure and antiwear properties of grease is denoted by extreme pressure and antiwear properties at this place.

In the present application, taking the loader as the example, the friction pair at point A, the friction pair at point S, or the friction pair at point Q is the positions where the unit areas receive the greatest pressures during the operation of the working device of the loader, and extreme pressure and antiwear properties of grease is most strictly demanded. By injecting different grease onto these friction pairs, carrying out the operation of the same intensity, and acquiring and analyzing the noise of each measuring point and the wear condition of the pin at point Q, extreme pressure and antiwear properties of different grease under the actual working condition can be well distinguished.

Many engineering machines, national defense equipments, and agricultural machines often operate at low rotational speed and a high load, and as a result, the higher extreme pressure and antiwear properties of grease is required. In the related art, the evaluation method of extreme pressure and antiwear properties of grease that all set at high rotational speed (>800 r/min) cannot be fully applied to many kinds of working conditions such as low speed, heavy load, and impact load. In this test method, the whole-vehicle-based test method of the engineering machine (rotational speed ≤20 r/min) is used to evaluate extreme pressure and antiwear properties of grease. The reliability of extreme pressure and antiwear properties index is improved.

Furthermore, the "10n % to (10n±2)%" of "the effective operation of the engineering machine under a load of 10n % to (10n±2)% rated load" needs to be treated with "about" to indicate certain errors necessarily resulting from the standard deviation found in specific testing processes.

In some embodiments, after the engineering machine operates effectively under the load of 10n % to (10n±2)% rated load, where the value of n is less than 15, whether the surface of the key pin is worn is observed and determined. In a case where the surface of the key pin is not worn, the value of n is increased and the engineering machine is caused to operate effectively under different loads. In a case where the surface of the key pin is worn, the test of the to-be-tested grease is stopped after the engineering machine completes operating effectively under the load. The whole-vehicle-based evaluation report of extreme pressure and antiwear properties of grease is issued according to the determination results of whether the surface of the key pin is worn under different loads.

The engineering machine generally operates effectively under a small load of a configured weight (for example, a load of 10%, 13%, 30% or 50% rated load) after the no-load operation of the engineering machine in the present application. When no wear or scratch occurs on the surface of the key pin during operating, it means that extreme pressure and antiwear properties of grease is relatively high. It is necessary to increase the load of the configured weight by changing the preceding the value of n, and then perform effective operation under a new load of a configured weight to determine whether the surface of the key pin is worn or scratched. Moreover, the whole-vehicle-based evaluation report of extreme pressure and antiwear properties of grease is issued according to the determination results of whether the surface of the key pin is worn under different loads. If there is no wear or scratch after operating under the higher load of a configured weight for the corresponding time, extreme pressure and antiwear properties of grease is better. Alternatively, the lower the scratch degree is, the better extreme pressure and antiwear properties of grease is.

From the perspective of protecting the engineering machine, the weight-configuration test exceeding a rated load of 150% of the engineering machine is not carried out in the test process of the present application, but this does not mean that the load of the configured weight cannot exceed a rated load of 150%. If the remaining operation steps are similar to those of the present application, the condition where only the load of the configured weight may be increased so as to exceed a rated load of 150%.

In some embodiments, the effective operating time of the key bearing pin of the engineering machine is [15, 30) min in a case where a range of the rated load is [0.1, 2) tons.

In some embodiments, the effective operating time of the key bearing pin of the engineering machine is [5, 15) min in a case where a range of the rated load is [2, 9) tons.

In some embodiments, the effective operating time of the bearing pin of the engineering machine is [0.5, 5) min in a case where a range of the rated load is [9, 80) tons.

The applicant adopts the mathematical symbols "(,)" and "[,]" in the preceding scheme to denote the opening or closing of the corresponding numerical range. For example, [2, 9) means that the left endpoint 2 of the range 2 to 9 is included, but the right endpoint 9 is not included. It should be noted, however, that the remaining scope, technical terms, or features of the application document should be understood in a manner well known to those skilled in the art unless otherwise specified.

In the present application, there is no obvious relationship between the effective operating time of the engineering machine and the rated load. However, the machine types with different loads of configured weights have different energy consumption during testing. For example, a larger machine type consumes more energy. In the process of the effective operation of such machine types, if the test time is longer, the energy consumption is higher, and the probability of errors is higher. According to the technical scheme in this application, the energy consumption can be reduced while the accuracy can also be improved to a preset degree.

In some embodiments, whether the abnormal noise occurs during the effective operation of the key pin under different loads is recorded. Moreover, the noise peak is acquired according to the following formula:

$$\text{Max}\left(\frac{dB_1 + dB_2 + dB_3 + dB_4 + dB_5}{5}, \frac{dB_x + dB_{x-1} + dB_{x-2} + dB_{x-3} + dB_{x-4}}{5}\right).$$

$dB_1$ to $dB_5$ denote the noise peaks of the first five times of lowering during about thirty times of lifting respectively. $dB_x$ to $dB_{x-4}$ denote the noise peaks of the last five times of lowering during the thirty times of lifting respectively.

In this application, in order to improve the accuracy of the evaluation method and reduce the human error in the process of determining scratches and wear. Optionally, during the effective operation of the engineering machine under a load of a configured weight, not only the wear and scratches must be observed, but also extreme pressure and antiwear properties of grease should be evaluated through the abnormal noise during operating. During the experiment, and during the effective operation of the key pin under different loads, if abnormal noise is caused, the test of the to-be-tested grease is stopped after the key pin completes operating effectively under the corresponding configured weight The extreme pressure and antiwear properties of the engineering machine during the effective operation is determined by recording whether the abnormal noise occurs and acquiring the noise peaks according to the preceding formula.

In the preceding formula, the average value of the noise peaks in the first five times of lowering and the average value of the noise peaks in the last five times of lowering during about thirty times of lifting under load at each stage are recorded and calculated. The maximum value of the two average values denotes the "noise peak".

There are many types of engineering machine. The noise peaks of devices under different types, different configurations, and different loads are different during the effective operation. In the present application, the range of the noise peak is 65 to 80 dB (A). Extreme pressure and antiwear properties of grease can be determined according to the range of the noise peak.

In the present application, an integrating-averaging sound level mete (acquisition time: 0.5 s) which meets the requirements of Level I in IEC 61672-1: 2002 is used as the instrument system to record the acquired data of the noise peak.

For the engineering machine in the present application, taking the loader as the example, the typical operation modes include crowding of the bucket, lifting of the working device, unloading, and lowering of the working device. In the actual working condition, the working device is subjected to the maximum load in the lifting process, and as a result, noise is most easily generated. The effective operation in the present application mainly refers to the lifting process. The lifting process includes two processes: lifting and lowering. Due to the high rotational speed of the engine during lifting, the noise in the lifting process is affected. During lowering, the engine is in an idle state, so the interference to the noise is small. Therefore, in order to accurately evaluate extreme pressure and antiwear properties of grease, the present application adopts a test method of acquiring the noise during the lowering of the working device without unloading after lifting.

Optionally, the whole-vehicle-based evaluation report of extreme pressure and antiwear properties of grease is issued according to the abnormal noise of the key pin during the effective operation under different loads, the noise peak, and the determination results of whether the surface of the key pin is worn.

Figure 6:
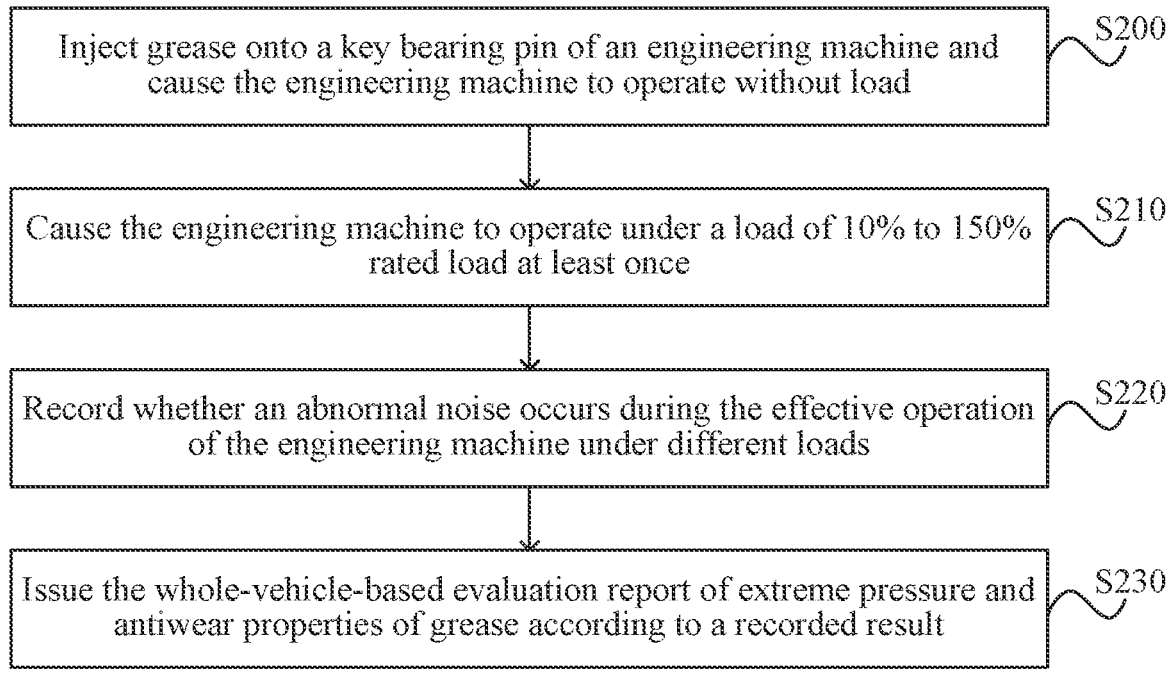
FIG. 6 is a flowchart illustrating a whole-vehicle-based method for evaluating extreme pressure and antiwear properties of grease according to an embodiment.

In an embodiment, as illustrated in FIG. 6, the whole-vehicle-based method for evaluating extreme pressure and antiwear properties of grease includes the steps described below.

In S200, the grease is injected onto the key bearing pin of the engineering machine, and the engineering machine is caused to operate without load.

In S210, the engineering machine is caused to operate under a load of 10% to 150% rated load at least once.

In S220, whether the abnormal noise occurs during the effective operation of the engineering machine under different loads is recorded.

In S230, the whole-vehicle-based evaluation report of extreme pressure and antiwear properties of grease is recorded according to the recorded result.

The engineering machine is caused to operate once under a load of 10% to 150% rated load for 0.5 min to 100 h.

Figure 7:
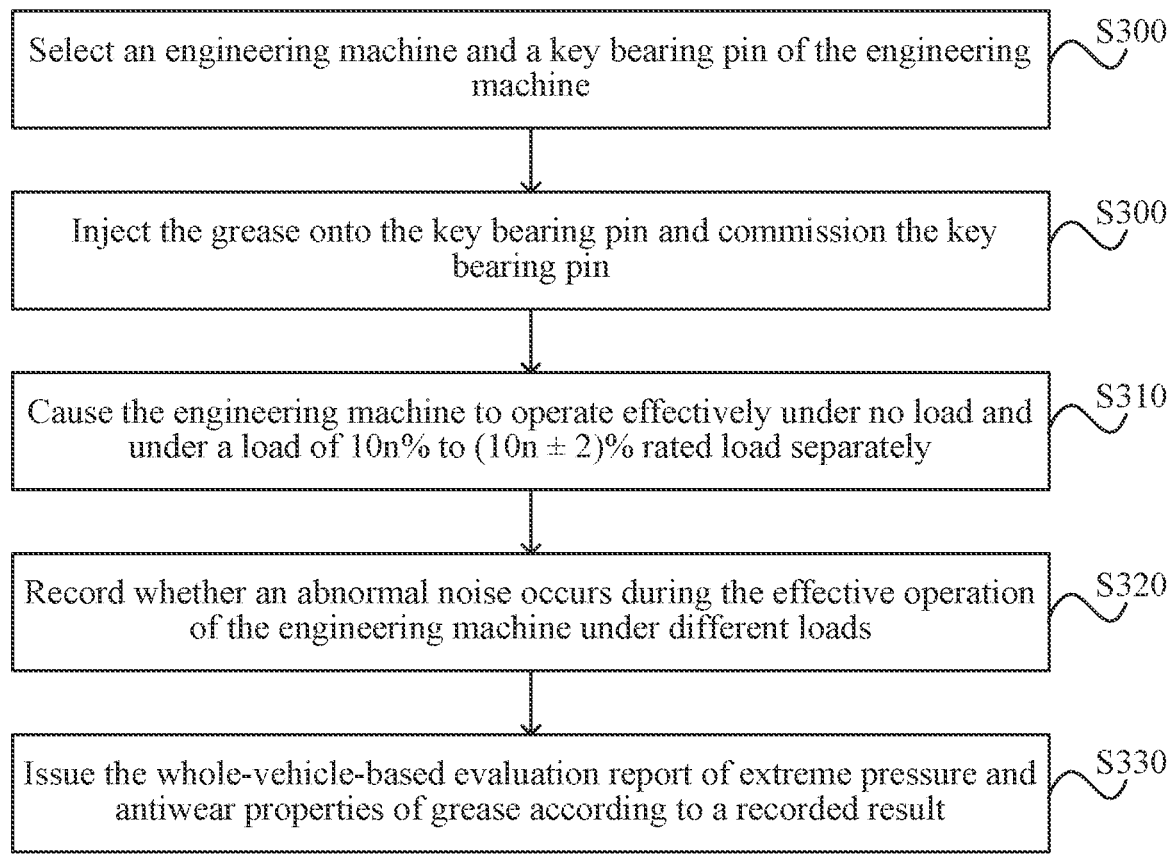
FIG. 7 is a flowchart illustrating a whole-vehicle-based method for evaluating extreme pressure and antiwear properties of grease according to an embodiment.

In an embodiment, as illustrated in FIG. 7, the whole-vehicle-based method for evaluating extreme pressure and antiwear properties of grease includes the steps described below.

In S300, the engineering machine and the key bearing pin of the engineering machine are selected.

In S310, the grease is injected onto the key bearing pin and the key bearing pin is commissioned.

In S320, the engineering machine is caused to operate effectively under no load and under a load of 10n % to (10n±2)% rated load separately.

In S330, whether the abnormal noise occurs during the effective operation of the engineering machine under different loads is recorded.

In S340, the whole-vehicle-based evaluation report of extreme pressure and antiwear properties of grease is issued according to the recorded result.

n denotes an integer of 1 to 15. The engineering machine is caused to operate once under a load of 10n % to (10n±2)% rated load for 0.5 min to 100 h.

The test results of the whole-vehicle-based evaluation method provided in the present application are described below.

The specific test procedure of the present application is described below.

In S10', the loader and the measuring point are selected.

In S20', ten or more times of no-load lifting are completed to ensure that the temperature of the hydraulic system reaches 45° C. to 50° C.

In S30', 280 g grease is injected onto each measuring point. Ten times of lifting under no load are completed to make the grease evenly distributed.

In S40', thirty times of lifting under no load, thirty times of lifting under the configured weight of (3000±20) kg, and thirty times of lifting under the configured weight of (5000±20) kg are completed in sequence.

In S50', the noise peak is acquired according to the following formula:

$$\text{Max}\left(\frac{dB_1 + dB_2 + dB_3 + dB_4 + dB_5}{5}, \frac{dB_x + dB_{x-1} + dB_{x-2} + dB_{x-3} + dB_{x-4}}{5}\right).$$

In S60', the wear condition at each measuring point is viewed. The report of extreme pressure and antiwear properties of grease is issued. The lifting process includes two processes: lifting and lowering.

The rated load of the loader in the S10' is 5000 kg.

Figure 3:
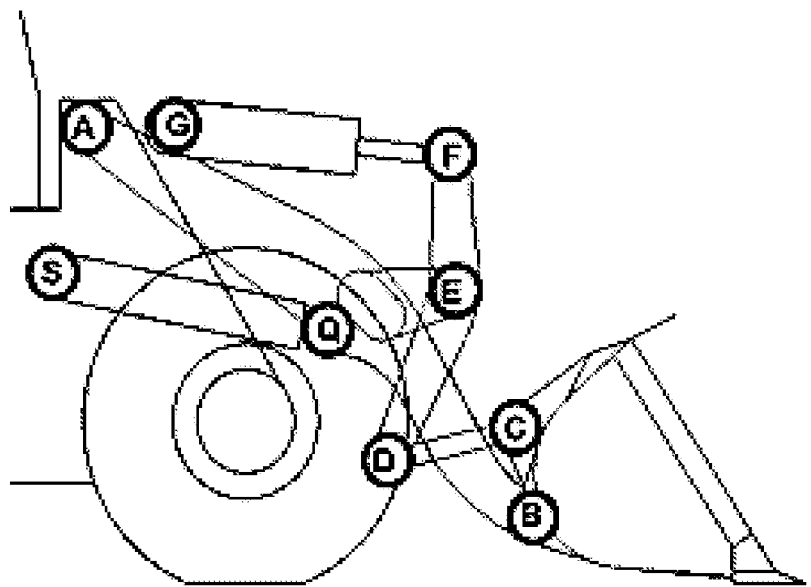
FIG. 3 is a view illustrating the structure of the hinge points of a working device of a loader according to the present application.

The working device of the loader in the S10' adopts a reversing six-bar linkage. Referring to FIG. 3, the hinge points of the reversing six-bar linkage are point A, point S, point Q, point B, point C, point D, point E, point F, and point G, respectively.

In the S10', the measuring points are point A, point S, and point Q of the reversing six-bar linkage, that is, the joint A between the movable arm and the front frame, the joint S between the movable arm cylinder and the front frame, and the joint Q between the movable arm and the movable arm cylinder.

In the S20', the time of once lifting under no load is 20±4 seconds, and the engine is controlled to be in the idle state during lowering.

In the S40', the movable arm rotates to the maximum position during lifting, and the rotation angle of the movable arm is 82° to 87°.

During lifting, the highest point of the movable arm is four meters from the ground.

The lifting process takes 12±2 S.

The lowering process takes 8±2 S.

In the S40', the first stage test (that is, thirty times of lifting under no load), the second stage test (that is, thirty times of lifting under the configured weight of (3000±20) kg), and the third stage test (that is, thirty times of lifting under the configured weight of (5000±20) kg) are completed in sequence.

If the abnormal noise occurs during the lowering of the working device when completing any time of lifting in the first stage test, the second stage test and the third stage test, the test of the to-be-tested grease is stopped immediately after the lifting of the corresponding stage test is completed. Otherwise, the lifting tests under all configured weights in the S40' are completed.

The preparation material of the pin is described below.

TABLE 2

Material of bearing pin

| Material of Pin | Material of Sleeve |
|---|---|
| 40Cr | 45/20CrMnTi |

After the testing, the joint Q is disassembled, and the wear condition of the key pin is observed. If there is an apparent wear scar on the surface of the pin (the length of the wear scar is greater than 1 cm) and the width or depth of the wear scar is greater than 3 mm, it is recorded as severe wear. The remaining phenomena are recorded as non-severe wear.

TABLE 3

Determination method of extreme pressure and antiwear properties

| Completed Test configured weight/ton | Whether Abnormal Noise Occurs | Noise Peak dB (A) | Wear Condition | Extreme pressure and antiwear properties Level |
|---|---|---|---|---|
| 0 | Yes | >74 | Severe wear | Failed |
|  |  |  | Non-severe wear | Failed |
|  |  | <74 | Severe wear | Failed |
|  |  |  | Non-severe wear | C |
| 3 | Yes | >74 | Severe wear | C |
|  |  |  | Non-severe wear | C |
|  |  | <74 | Severe wear | C |
|  |  |  | Non-severe wear | B |
| 5 | Yes | >74 | Severe wear | B |
|  |  |  | Non-severe wear | B |
|  |  | <74 | Severe wear | B |
|  |  |  | Non-severe wear | A |
|  | No | >74 | Severe wear | B |
|  |  |  | Non-severe wear | A |
|  |  | <74 | Severe wear | A |
|  |  |  | Non-severe wear | A |

Precision and deviation: the reliability of the test results (95% confidence level) is determined according to the following provisions.

The difference between the two test results continuously measured on the same sample cannot exceed one extreme pressure and antiwear properties level, in a case where the same operator uses the same test device and follows the same method in the same experimental site.

The difference between the two single and independent results measured on the same sample cannot exceed one extreme pressure and antiwear properties level, in a case where different operators use different test devices and follow the same method in different experimental sites.

In an embodiment, the grease in the S30' includes the grease B and the grease C, and each grease completes all the tests in the S40'.

Figure 1:
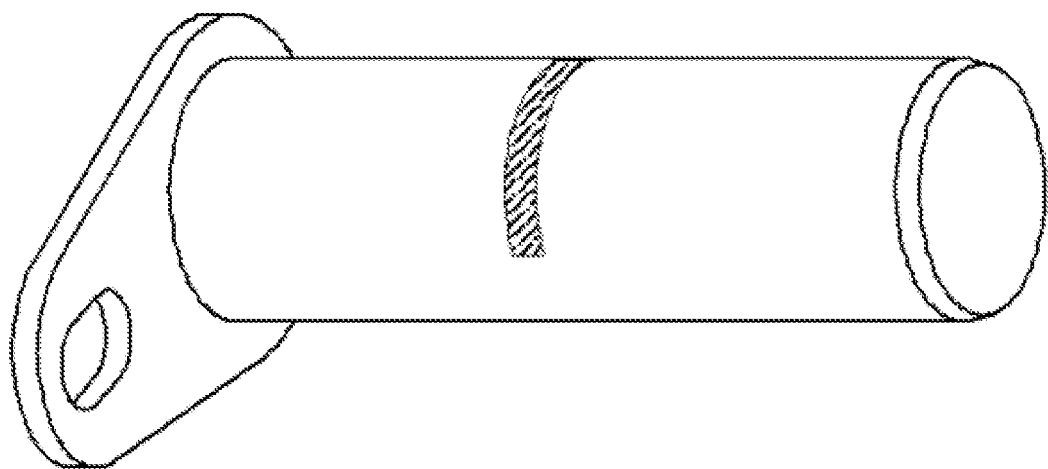
FIG. 1 is a view illustrating the wear condition of a key bearing pin with grease B according to the present application.
Figure 2:
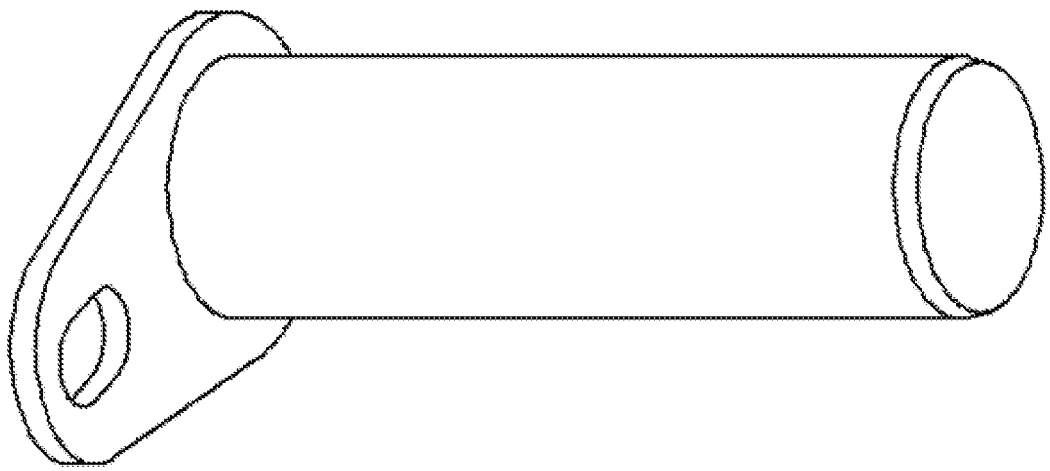
FIG. 2 is a view illustrating the wear condition of a key bearing pin with grease C according to the present application.

The preliminary test results are described below (refer to FIGS. 1 and 2).

TABLE 4

Preliminary test result

|  | Abnormal Noise Record | Wear Condition | Noise Peak dB (A) |
|---|---|---|---|
| Grease B | Yes | Severe wear | 69.12 |
| Grease C | No | Non-severe wear | 67.65 |

According to the disassembly condition of the friction pair pin at point Q, the grease C has better extreme pressure and antiwear properties. The capacity can improve the reliability of the vehicle.

In an embodiment, extreme pressure and antiwear properties of grease B and extreme pressure and antiwear properties of grease C in the preceding embodiment are tested by using the four-ball evaluation method in the related art.

The test results are shown in the table below.

TABLE 5

Test result

|  | PD/kgf (Four-ball Sintering Load) |
|---|---|
| Grease B | 250 |
| Grease C | 250 |

It can be seen that it is difficult to distinguish extreme pressure and antiwear properties of grease B and extreme pressure and antiwear properties of grease C by the four-ball evaluation method in the related art. Using the method of the present application, the two kinds of grease complete the whole-vehicle-based test under the load of 5000±20 kg respectively and exhibit different conditions of whether there is an abnormal noise or not and different numerical values of the noise peaks. Therefore, the grease C can provide better comfort to the customer.

Embodiment One

In S10', the loader and the measuring point are selected.

In S20', ten or more times of lifting under no load are completed to ensure that the temperature of the hydraulic system reaches 45° C. to 50° C.

In S30', 280 g of the grease B is injected onto each measuring point. Ten times of lifting under no load are completed to make the grease evenly distributed.

In S40', fifteen times of lifting under the configured weight of (5000±20) kg are completed and the abnormal noise of the loader is recorded.

In S50', 280 g grease C is injected onto each measuring point, and ten times of lifting under no load are completed to make the grease evenly distributed.

In S60', the S40' is repeated.

In S70', the evaluation report of extreme pressure and antiwear properties of grease is issued according to the abnormal noise.

The lifting process includes two processes: lifting and lowering. The rated load of the loader in the S10' is 5000 kg. The working device of the loader in the S10' adopts the reversing six-bar linkage. Referring to FIG. 3, the hinge points of the reversing six-bar linkage are point A, point S, point Q, point B, point C, point D, point E, point F, and point G, respectively. In the S10', the measuring points are point A, point S, and point Q of the reversing six-bar linkage, that is, the joint A between the movable arm and the front frame, the joint S between the movable arm cylinder and the front frame, and the joint Q between the movable arm and the movable arm cylinder.

In the S20', the time of once lifting under no load is 20±4 seconds, and the engine is controlled to be in the idle state during lowering.

In the S40', the movable arm rotates to the maximum position during lifting, and the rotation angle of the movable arm is 82° to 87°.

During lifting, the highest point of the movable arm is four meters from the ground.

The lifting process takes 12±2 S. The lowering process takes 8±2 S.

The preparation material of the pin is described below.

TABLE 6

Material of bearing pin

| Material of Pin | Material of Sleeve |
|---|---|
| 40Cr | 45/20CrMnTi |

TABLE 7

Evaluation method of extreme pressure and antiwear properties - abnormal noise conditions

| Grease Type | Abnormal Noise |
|---|---|
| B | Yes |
| C | No |

Embodiment Two

In S10', the loader and the measuring point are selected.

In S20', ten or more times of lifting under no load are completed to ensure that the temperature of the hydraulic system reaches 45° C. to 50° C. In S30', 280 g grease B is injected onto each measuring point. Ten times of lifting under no load are completed to make the grease evenly distributed.

In S40', thirty times of lifting under the configured weight of (5000±20) kg are completed, and sound pressure levels during lifting are recorded.

In S50', 280 g grease C is injected onto each measuring point, and ten times of lifting under no load are completed to make the grease evenly distributed.

In S60', the S40' is repeated.

In S70', the noise peak is acquired according to the following formula:

$$\text{Max}\left(\frac{dB_1 + dB_2 + dB_3 + dB_4 + dB_5}{5}, \frac{dB_x + dB_{x-1} + dB_{x-2} + dB_{x-3} + dB_{x-4}}{5}\right).$$

In S80', the evaluation report of extreme pressure and antiwear properties of grease is issued according to the magnitude of the noise peak.

The lifting process includes two processes: lifting and lowering.

The rated load of the loader in the S10' is 5000 kg.

The working device of the loader in the S10' adopts the reversing six-bar linkage. Referring to FIG. 3, the hinge points of the reversing six-bar linkage are point A, point S, point Q, point B, point C, point D, point E, point F, and point G, respectively.

In the S10', the measuring points are point A, point S, and point Q of the reversing six-bar linkage, that is, the joint A between the movable arm and the front frame, the joint S between the movable arm cylinder and the front frame, and the joint Q between the movable arm and the movable arm cylinder.

In the S20', the time of once lifting under no load is 20±4 seconds, and the engine is controlled to be in the idle state during lowering. In the S40', the movable arm rotates to the maximum position during lifting, and the rotation angle of the movable arm is 82° to 87°.

During lifting, the highest point of the movable arm is four meters from the ground.

The sound pressure levels in S40' are recorded with reference to GB/T 25614. The lifting process takes 12±2 S. The lowering process takes 8±2 S.

The preparation material of the pin is described below.

TABLE 8

Material of bearing pin

| Material of Pin | Material of Sleeve |
|---|---|
| 40Cr | 45/20CrMnTi |

TABLE 9

Evaluation method of extreme pressure and antiwear properties - noise peak dB (A)

| Grease Type | Noise Peak dB (A) |
|---|---|
| B | 69.12 |
| C | 67.65 |

Embodiment Three

In S10', the loader and the measuring point are selected.

In S20', ten or more times of lifting under no load are completed to ensure that the temperature of the hydraulic system reaches 45° C. to 50° C.

In S30', 280 g grease B is injected onto each measuring point. Ten times of lifting under no load are completed to make the grease evenly distributed.

In S40', thirty times of lifting under the configured weight of (5000±20) kg are completed and the sound pressure levels during lifting are recorded.

In S50', 280 g grease C is injected onto each measuring point, and ten times of lifting under no load are completed to make the grease evenly distributed.

In S60', the S40' is repeated.

In S70', instantaneous sound power levels are calculated in accordance with the requirement of GB/T 25614.

In S80', the sound power level peak is acquired according to the following formula:

$$\text{Max}\left(\frac{dB_1 + dB_2 + dB_3 + dB_4 + dB_5}{5}, \frac{dB_x + dB_{x-1} + dB_{x-2} + dB_{x-3} + dB_{x-4}}{5}\right).$$

In S90', the whole-vehicle-based evaluation report of extreme pressure and antiwear properties of grease is issued according to the magnitude of the sound power level peak.

The lifting process includes two processes: lifting and lowering.

The rated load of the loader in the S10' is 5000 kg.

The working device of the loader in the S10' adopts the reversing six-bar linkage. Referring to FIG. 3, the hinge points of the reversing six-bar linkage are point A, point S, point Q, point B, point C, point D, point E, point F, and point G, respectively.

In the S10', the measuring points are point A, point S, and point Q of the reversing six-bar linkage, that is, the joint A between the movable arm and the front frame, the joint S between the movable arm cylinder and the front frame, and the joint Q between the movable arm and the movable arm cylinder.

In the S20', the time of once lifting under no load is 20±4 seconds, and the engine is controlled to be in the idle state during lowering.

In the S40', the movable arm rotates to the maximum position during lifting, and the rotation angle of the movable arm is 82° to 87°.

During lifting, the highest point of the movable arm is four meters from the ground.

The sound pressure levels in S40' are recorded with reference to GB/T 25614.

The lifting process takes 12±2 S.
The lowering process takes 8±2 S.
The preparation material of the pin is described below.

TABLE 10

| Material of bearing pin | |
|---|---|
| Material of Pin | Material of Sleeve |
| 40Cr | 45/20CrMnTi |

TABLE 11

| Evaluation method of extreme pressure and antiwear properties - sound power level Peak dB (A) | |
|---|---|
| Grease Type | Sound Power Level Peak dB (A) |
| B | 101.6 |
| C | 100.5 |

Embodiment Four

In S10', the loader and the measuring point are selected.

In S20', ten or more times of lifting under no load are completed to ensure that the temperature of the hydraulic system reaches 45° C. to 50° C.

In S30', 280 g grease B is injected onto each measuring point. Ten times of lifting under no load are completed to make the grease evenly distributed.

In S40', thirty times of lifting under no load, thirty times of lifting under the configured weight of (3000±20) kg, and thirty times of lifting under the configured weight of (5000±20) kg are completed in sequence.

In S50', the wear condition at each measuring point is viewed. The evaluation report of extreme pressure and antiwear properties of grease is issued.

The lifting process includes two processes: lifting and lowering.

The rated load of the loader in the S10' is 5000 kg.

The working device of the loader in the S10' adopts the reversing six-bar linkage. Referring to FIG. 3, the hinge points of the reversing six-bar linkage are point A, point S, point Q, point B, point C, point D, point E, point F, and point G, respectively.

In the S10', the measuring points are point A, point S, and point Q of the reversing six-bar linkage, that is, the joint A between the movable arm and the front frame, the joint S between the movable arm cylinder and the front frame, and the joint Q between the movable arm and the movable arm cylinder.

In the S20', the time of once lifting under no load is 20±4 seconds, and the engine is controlled to be in the idle state during lowering.

In the S40', the movable arm rotates to the maximum position during lowering, and the rotation angle of the movable arm is 82° to 87°.

During lifting, the highest point of the movable arm is four meters from the ground.

The lifting process takes 12±2 S.

The lowering process takes 8±2 S.

In the S40', the first stage test (that is, thirty times of lifting under no load), the second stage test (that is, thirty times of lifting under the configured weight of (3000±20) kg), and the third stage test (that is, thirty times of lifting under the configured weight of (5000±20) kg) are completed in sequence.

If the abnormal noise occurs during the lowering of the working device when completing any time of lifting in the first stage test, the second stage test, and the third stage test, the test of the to-be-tested grease is stopped immediately after the lifting of the corresponding stage test is completed. Otherwise, the lifting tests under all configured weights in the S40' are completed.

The preparation material of the pin is described below.

TABLE 12

| Material of bearing pin | |
|---|---|
| Material of Pin | Material of Sleeve |
| 40Cr | 45/20CrMnTi |

After the testing, the joint Q is disassembled, and the wear condition of the key pin is observed. If there is the apparent wear scar on the surface of the pin (the length of the wear scar is greater than 1 cm) and the width or depth of the wear scar is greater than 3 mm, it is recorded as severe wear. The remaining phenomena are recorded as non-severe wear.

TABLE 13

| Evaluation method of extreme pressure and antiwear properties - wear condition of key pin | |
|---|---|
| Grease Type | Wear Condition |
| B | Severe Wear |
| C | Non-severe Wear |

What is claimed is:

1. A whole-vehicle-based method for evaluating extreme pressure and antiwear properties of grease, comprising:

injecting the grease onto a key bearing pin of an engineering machine and causing the engineering machine to operate without load;

causing the engineering machine to operate under a load of 10% to 150% rated load at least once;

viewing and analyzing a wear condition of a surface of the key bearing pin; and issuing a whole-vehicle-based evaluation report of the extreme pressure and antiwear properties of the grease, wherein the engineering machine is caused to operate once under the load of 10% to 150% rated load for 0.5 min to 100 h, wherein the method further comprises:

recording whether an abnormal noise occurs during effective operation of the key bearing pin under different loads, and determining a noise peak generated under a corresponding load according to a formula:

$$\text{Max}\left(\frac{dB_1 + dB_2 + dB_3 + dB_4 + dB_5}{5}, \frac{dB_x + dB_{x-1} + dB_{x-2} + dB_{x-3} + dB_{x-4}}{5}\right),$$

wherein $$\frac{dB_1 + dB_2 + dB_3 + dB_4 + dB_5}{5}$$

denotes an average value of noise peaks of the key bearing pin during first five times of lowering in N times of lifting of a working device of the engineering machine, and $$\frac{dB_x + dB_{x-1} + dB_{x-2} + dB_{x-3} + dB_{x-4}}{5}$$

denotes an average value of noise peaks of the key bearing pin during last five times of lowering in the N times of lifting of the working device of the engineering machine.

2. The whole-vehicle-based method for evaluating the extreme pressure and antiwear properties of the grease of claim 1, wherein a range of the rated load of the engineering machine is 0.1 to 80 tons.

3. The whole-vehicle-based method for evaluating the extreme pressure and antiwear properties of the grease of claim 2, wherein effective operating time of the key bearing pin is [15, 30) min in a case where a range of the rated load of the engineering machine is [0.1, 2) tons.

4. The whole-vehicle-based method for evaluating the extreme pressure and antiwear properties of the grease of claim 2, wherein effective operating time of the key bearing pin is [5, 15) min in a case where a range of the rated load of the engineering machine is [2, 9) tons.

5. The whole-vehicle-based method for evaluating the extreme pressure and antiwear properties of the grease of claim 2, wherein effective operating time of the key bearing pin is [0.5, 5) min, in a case where a range of the rated load of the engineering machine is [9, 80) tons.

6. The whole-vehicle-based method for evaluating the extreme pressure and antiwear properties of the grease of claim 1, wherein the engineering machine is caused to operate once under the load of 10% to 150% rated load for 0.5 min to 30 min.

7. The whole-vehicle-based method for evaluating the extreme pressure and antiwear properties of the grease of claim 1, in response to the abnormal noise occurring during the effective operation of the key bearing pin, a test of to-be-tested grease is stopped after the effective operation of the key bearing pin under the corresponding load is completed.

8. The whole-vehicle-based method for evaluating the extreme pressure and antiwear properties of the grease of claim 7, wherein issuing the whole-vehicle-based evaluation report of the extreme pressure and antiwear properties of the grease comprises: issuing the whole-vehicle-based evaluation report of the extreme pressure and antiwear properties of the grease according to the abnormal noise of the key bearing pin during effective operation under the different loads, the noise peak, and a determination result of whether the surface of the key bearing pin is worn.

9. A whole-vehicle-based method for evaluating extreme pressure and antiwear properties of grease, comprising:

selecting an engineering machine and a key bearing pin of the engineering machine;

injecting the grease onto the key bearing pin and commissioning the key bearing pin;

causing the engineering machine to operate effectively under no load and under a load of 10n % to (10n±2)% rated load separately;

viewing and analyzing a wear condition of the key bearing pin; and issuing an evaluation report of the extreme pressure and antiwear properties of the grease, wherein n denotes an integer of 1 to 15, and the engineering machine is caused to operate once under a load of 10n % to (10n±2)% the rated load for 0.5 min to 100 h, wherein the method further comprises:

recording whether abnormal noise occurs during effective operation of the engineering machine under different loads, and recording a noise peak of the engineering machine during the effective operation under the different loads, wherein a noise peak generated under a corresponding load is determined according to a formula:

$$\text{Max}\left(\frac{dB_1 + dB_2 + dB_3 + dB_4 + dB_5}{5}, \frac{dB_x + dB_{x-1} + dB_{x-2} + dB_{x-3} + dB_{x-4}}{5}\right),$$

wherein $$\frac{dB_1 + dB_2 + dB_3 + dB_4 + dB_5}{5}$$

denotes an average value of noise peaks of the key bearing pin during first five times of lowering in N times of lifting of a working device of the engineering machine, and $$\frac{dB_x + dB_{x-1} + dB_{x-2} + dB_{x-3} + dB_{x-4}}{5}$$

denotes an average value of noise peaks of the key bearing pin during last five times of lowering in the N times of lifting of the working device of the engineering machine.

10. The whole-vehicle-based method for evaluating the extreme pressure and antiwear properties of the grease of claim 9, wherein in response to an abnormal noise of the engineering machine occurring during an effective operation of the key bearing pin, after the effective operation of the key bearing pin under a corresponding load is completed, a test of to-be-tested grease is stopped, and the whole-vehicle-based evaluation report of the extreme pressure and antiwear properties of the grease is issued.

* * * * *